United States Patent [19]

Socci et al.

[11] Patent Number: 4,832,944
[45] Date of Patent: May 23, 1989

[54] NAIL ENAMEL CONTAINING SILICONE-COATED PIGMENTS

[75] Inventors: Robert L. Socci, Cedar Grove, N.J.; Anatoly A. Ismailer, Forest Hills, N.Y.; Anthony Castrogiovanni, Belford, N.J.

[73] Assignee: Revlon Inc., New York, N.Y.

[21] Appl. No.: 938,329

[22] Filed: Dec. 3, 1986

Related U.S. Application Data

[63] Continuation of Ser. No. 538,601, Oct. 3, 1983, abandoned.

[51] Int. Cl.$^4$ .............................. A61K 7/04
[52] U.S. Cl. ...................... 424/61; 106/417; 106/447; 106/414; 106/499
[58] Field of Search ............... 424/61; 106/308 Q

[56] References Cited

U.S. PATENT DOCUMENTS

| | | |
|---|---|---|
| 2,615,006 | 10/1952 | Lane . |
| 2,717,246 | 9/1955 | Kienle et al. . |
| 3,025,179 | 3/1962 | Holbein . |
| 3,864,294 | 2/1975 | Busch . |
| 4,061,503 | 12/1977 | Berger et al. ............ 106/300 |
| 4,158,053 | 7/1979 | Greene et al. ............ 424/61 |
| 4,166,110 | 8/1979 | Isobe et al. ............... 424/61 |
| 4,302,442 | 11/1981 | Socci et al. . |
| 4,342,742 | 8/1982 | Sebag et al. ............ 424/59 |
| 4,344,799 | 8/1982 | Köhler et al. ........... 106/300 |
| 4,578,266 | 3/1986 | Tietjen et al. . |

FOREIGN PATENT DOCUMENTS

| | | |
|---|---|---|
| 1125659 | 6/1982 | Canada ...................... 424/68 |
| 0133963 | 3/1985 | European Pat. Off. . |
| 1012729 | 7/1957 | Fed. Rep. of Germany ........ 424/69 |
| 2205557 | 5/1974 | France . |
| 5139316 | 10/1980 | Japan ......................... 424/61 |
| 56-29512 | 3/1981 | Japan ......................... 424/63 |

OTHER PUBLICATIONS

Ashmead et al., J. Oil Col. Chem. Assoc. 1971, 54, 403–424.
Kirk-Othmer, Encyclopedia of Chemical Technology, 3rd Ed., Supplement vol., Wiley, New York, pp. 339–340.
Chemical Abstracts, vol. 95 (1981), No. 95:12586v.
Chemical Abstracts, vol. 94, No. 6, Feb. 1981, p. 358, No. 36125z, Columbus, OH, U.S.; & JP-A-80135213 (Polar Chemicals Ltd.) 23-10-1980 *Absract*.
Seifen-Ole-Fette-Wachse, vol. 109, No. 9, Jun. 1983, p. 271, Augsburg, DE, "Filbildner und Weichmacher für Nagellacke* Gelzubereitung und deren Verwendung in Nagellacker"* and English Translation.
Patents Abstract of Japan, vol. 8, No. 273 (C-256) [1710], 13th Dec. 1984; & JP-A-59 144 709 (Pola Kasei Kogyo K.K.) 18-08-1984 *Abstract*.

*Primary Examiner*—Sam Rosen
*Attorney, Agent, or Firm*—Synnestvedt & Lechner

[57] ABSTRACT

Pigmented nail enamels in which the pigment is coated with an organo-polysiloxane exhibit greatly reduced settling and migration of the pigment.

17 Claims, No Drawings

NAIL ENAMEL CONTAINING SILICONE-COATED PIGMENTS

CROSS-REFERENCE TO RELATED APPLICATION

This is a continuation of U.S. application Ser. No. 538,601, filed Oct. 3, 1983, now abandoned.

BACKGROUND OF THE INVENTION

This invention relates to nail enamels. It particularly relates to nail enamels which are substantially free of the settling and the migration of the pigment and other materials suspended in the composition.

Conventional nail enamel compositions incorporate in their formulas a montmorillonite clay as a gellant to suspend pigments and pearlescent materials contained therein.

To achieve desired properties for these systems, as much as 2.0% or more of the gellant is recommended to effect complete and stable suspension. The use of larger amounts of the gellant in a nail enamel composition adversely affects the application and flow properties of the preparation. When the levels of the gellant are reduced to about 0.5-1.25%, other additives must then be added to maintain desired suspension and performance characteristics. It is also known that nail enamel compositions exhibit pigment migration, i.e., preferential separation, flocculation and flotation as distinguished from settling. While migration does not affect the performance of the nail enamel, the streaking effects noticeable from such migration are aesthetically undesirable.

U.S. Pat. No. 4,166,110 discloses a nail enamel which contains an organically substituted polysiloxane to render the enamel film easily strippable from the nail. The patent does not discuss how to incorporate pigments into such a formulation, and does not suggest coating pigments with the polysiloxane.

An article by B. V. Ashmead et al., "The Silicone Treatment of Titania", J. Oil Col. Chem. Assoc., Vol. 54 (1971), pp. 403-424, discusses the adsorption of various silicone polymers onto the surface of titanium dioxide and discloses that silicone treated pigments disperse better in coventional paint media than untreated pigments. This disclosure does not suggest how coated pigments would behave in the solvent system employed in nail enamels. Moreover, the emphasis on dispersion, i.e. the length of time one needs to stir the paint in order to disperse the pigment in the surrounding media, does not support any suggestion as to how quickly the pigment settles and/or migrates once stirring is stopped. Indeed, freedom from settling and migration is of little or no concern to paint manufacturers, because the paint is in a non-transparent can until the user opens the can, stirs the paint, and applies the paint. By contrast, freedom from settling and migration even without stirring are of vital concern to the nail enamel manufacturer, who customarily sells the enamel in a transparent bottle, because the customer must be persuaded to buy the enamel based on how the enamel looks in the bottle.

BRIEF SUMMARY OF THE INVENTION

In accordance with the present invention, a pigmented nail enamel is provided which is substantially free from settling and migration of the pigment contained therein, in which the nail enamel contains an inorganic pigment which is coated with an organically substituted polysiloxane. The improved nail enamel is prepared by coating the pigment with the polysiloxane before mixing the coated pigment with the remaining components of the nail enamel.

DETAILED DESCRIPTION OF THE INVENTION

As indicated, the pigmented nail enamels contain pigment which has been coated with organically substituted polysiloxane.

The polysiloxane coating is generally characterized in that it imparts to the pigment the desirable properties mentioned herein when formulated into a nail enamel. While we do not intend to be bound by any particular specific definition for the coating, we use the term "polysiloxane" to include polymeric chains having up to 100 or even to 1,000 repeating (Si—O) units, wherein at least one Si atom of each chain is linked to the pigment surface through an oxygen atom. The chains can be cross-linked to each other as well. The remaining functional sites of each Si atom in the chain can be occupied by hydrogen, methyl, $C_2$-$C_{30}$ alkyl or alkenyl, and/or phenyl, and equivalents thereof, resulting in units such as $-\!\!+\!\!Si(CH_3)(C_6H_5)O\!\!+\!\!-$, $-\!\!+\!\!Si(CH_3)(H)O\!\!+\!\!-$, or $-\!\!+\!\!Si(H)(C_6H_5)O\!\!+\!\!-$, and generally capped with $-Si(CH_3)_3$.

Satisfactory colors can be obtained in a variety of pigments from Clarks Colors for whom the sole known distributor is Whittaker, Clark & Daniels, Inc. The product has the trade name "Hydrophobes". Alternatively, one can make the coated pigment by, for instance, reacting the uncoated pigment with (A) a silane of the formula $A_1SiX_1X_2X_3$, wherein $A_1$ is alkyl or alkenyl having up to 30 carbon atoms and $X_1$, $X_2$ and $X_3$ are independently chloro, methoxy or ethoxy; (B) $(CH_3)_3SiO\!\!+\!\!Si(CH_3)_2O\!\!+\!\!_nSi(CH_3)_2OA_2$ wherein n is 1 to 100 or up to 1,000, and $A_2$ is $C_1$-$C_{30}$ alkyl; or (C)$(CH_3)_3SiO\!\!+\!\!Si(CH_3)(H)O\!\!+\!\!_pSi(CH_3)_3$ wherein p is 1 to 100 or up to 1,000. The reaction conditions are chosen so that $X_1$, $X_2$, $X_3$, $A_2$, or (H), as the case may be, hydrolyzes and bonds to the pigment surface through oxygen atoms. This mechanism, and determination of appropriate reaction conditions, are familiar matters to the chemist.

The pigment which is incorporated within the coating can be any cosmetically acceptable inroganic or organic pigment. Examples of such pigments include: iron oxides, titanated mica, iron oxide coated mica, titanium dioxide (e.g. rutile, anatase), ultramarine, chromium oxide, chromium hydroxide, manganese violet, and their equivalents. Preferred pigments from the above list are iron oxide and titanium dioxide.

The organo-polysiloxane-coated pigment can in general comprise up to about 10 wt. % of the nail enamel product. More preferably, the coated pigment comprises up to about 2 wt. %, and even more preferably it comprises about 1 wt. % to about 2 wt. %.

Nail enamels which contain the coated pigments set forth above exhibit greatly reduced settling and migration compared to enamels which are identical except for lacking the silicone coating on the pigment.

In addition to the coated pigment, the nail enamel contains an otherwise conventional base, including nitrocellulose, solvent, and suspending agent. The base can also include a resin and a plasticizer.

The resin should be one which adds to the durability, adhesion, and gloss of the enamel. Examples of preferred resins include toluene sulfonamide formaldehyde resin, and polyesters. The plasticizer should be effective to aid the enamel coating's flexibility. Examples of preferred plasticizers include dibutyl phthalate and dioctyl phthalate. The solvent should dissolve the other components of the base, allowing the enamel to flow onto the nail, and should be able to evaporate from the nail. Examples of preferred solvents include toluene, isopropanol, butyl acetate, ethyl acetate, and mixtures thereof. The suspending agent should help suspend the pigments in the base. Examples of preferred supending agents include montmorillonite clays.

A more complete listing of conventional bases which are useful with this invention can be found in standard sources well-known to the chemist, such as *Cosmetics, Science and Technology,* Balsam and Sagarin (eds.), 2nd Edition (1972), Vol. 2, Chapter 29 (Wiley Interscience, New York, N.Y.).

The coated pigment can be dispersed into the other nail enamel components readily by conventional mixing techniques employed in nail enamel manufacture, for example, chipping, roller milling, etc.

The superior effect of the present invention is seen in the following comparative examples. These examples are illustrative only and should not be construed as limiting. The numerical evaluation ratings have the following meanings:

5. Excellent—no visible signs of pigment migration or settling.
4. Good—Very slight settling observed, no signs of pigment migration.
3. Average—Some settling and very slight pigment migration.
2. Poor—Settling and migration readily apparent (not saleable).
1. Unacceptable—Very bag settling and migration (not saleable).

In the following tables where pigment is indicated as "treated" it had been coated with poly(methylhydrogen)siloxane obtained from Clark Colors with the product number 9454 for the coated iron oxide, and product number 9428 for the coated titanium dioxide. The amounts of treated pigment were chosen to provide equal amounts of pigment per se in all four samples.

All amounts are in percent by weight.

EXAMPLE 1

Four samples of a nail enamel ("Ripe Plum") were prepared by mixing uniformly the ingredients indicated in Table 1. The products were compared for settling and migration after holding test amounts thereof for two months without agitation, some at room temperature and some at 120° F.

TABLE 1

| Sample No.: | 1 | 2 | 3 | 4 |
|---|---|---|---|---|
| Nitrocellulose | 15.00 | 15.00 | 15.00 | 15.00 |
| Dibutylphthalate | 4.50 | 4.50 | 4.50 | 4.50 |
| Toluene sulfonamide formaldehyde resin | 6.00 | 6.00 | 6.00 | 6.00 |
| Butyl acetate | 30.00 | 30.00 | 30.00 | 30.00 |
| Ethyl acetate | 8.00 | 8.00 | 8.00 | 8.00 |
| Toluene | 26.00 | 26.00 | 26.00 | 26.00 |

TABLE 1-continued

| Sample No.: | 1 | 2 | 3 | 4 |
|---|---|---|---|---|
| Isopropanol | 7.35 | 7.35 | 7.59 | 7.59 |
| Bentone 27 (montmorillorite) | 1.00 | 1.00 | 1.00 | 1.00 |
| Titanium dioxide (treated) | 1.00 | 1.00 | — | — |
| Iron oxide (treated) | 0.48 | — | 0.48 | — |
| Titanium dioxide (untreated) | — | — | 0.76 | 0.76 |
| Iron oxide (untreated) | — | 0.48 | — | 0.48 |
| Untreated organic pigments (mixture of D & C Red 7 and ferric ammonium ferrocyanide) | 0.67 | 0.67 | 0.67 | 0.67 |
| Observation after 2 mos. | | | | |
| at room temp. | 5 | 4 | 4 | 4 |
| at 120° F | 5 | 3 | 3 | 3 |

EXAMPLE 2

Four samples of nail enamel ("Carmel") were prepared by mixing uniformly the ingredients indicated in Table 2. The products were compared for settling and migration after holding test amounts thereof for two months without agitation, some at room temperature and some at 120° F.

TABLE 2

| Sample No.: | 1 | 2 | 3 | 4 |
|---|---|---|---|---|
| Nitrocellulose | 15.00 | 15.00 | 15.00 | 15.00 |
| Dibutylphthalate | 4.50 | 4.50 | 4.50 | 4.50 |
| Toluene sulfonamide formaldehyde resin | 6.00 | 6.00 | 6.00 | 6.00 |
| Butyl acetate | 30.00 | 30.00 | 30.00 | 30.00 |
| Ethyl acetate | 8.00 | 8.00 | 8.00 | 8.00 |
| Toluene | 26.00 | 26.00 | 26.00 | 26.00 |
| Isopropanol | 8.327 | 8.327 | 9.517 | 9.517 |
| Bentone 27 (montmorillorite) | 1.00 | 1.00 | 1.00 | 1.00 |
| Titanium dioxide (treated) | 0.79 | 0.79 | — | — |
| Iron oxide (treated) | 0.35 | — | 0.35 | — |
| Titanium dioxide (untreated) | — | — | 0.60 | 0.60 |
| Iron oxide (untreated) | — | 0.35 | — | 0.35 |
| Untreated organic pigments (mixture of D & C Yellow 5, D & C Red 6, and ferric ammonium ferrocyanide) | 0.033 | 0.033 | 0.033 | 0.033 |
| Observation after 2 mos. | | | | |
| at room temp. | 5 | 4 | 4 | 4 |
| at 120° F. | 5 | 3 | 3 | 3 |

The observations in Tables 1 and 2 indicate that nail enamels in which all inorganic pigments were coated with the organopolysiloxane were superior to enamels in which some, or all, inorganic pigments were not so coated.

What is claimed is:

1. In a nail enamel which contains a plurality of pigments, including at least one inorganic pigment, and a liquid base and suspending agent for holding pigment in suspension, the improvement wherein said inorganic pigment has a coating consisting of organically substituted polysiloxanes which are chemically bonded to the pigment surface, wherein said enamel exhibits reduced settling and migration of the pigment contained therein compared to an enamel which is identical except for lacking said chemically bonded coating.

2. The nail enamel of claim 1 wherein said coated pigment comprises up to about 10 wt. % of the nail enamel.

3. The nail enamel of claim 1 wherein said coated pigment comprises up to about 2 wt. % of the nail enamel.

4. The nail enamel of claim 1 wherein said coating, when bonded to said pigment surface, has 1–1000 (Si—O) units in whih the remaining functional sites of each Si atom are substituted with hydrogen, methyl, $C_2$–$C_{30}$ alkyl, $C_2$–$C_{30}$ alkenyl, or phenyl, provided that at least one Si atom of the polysiloxanes is chemically bonded to an oxygen atom which is bonded to the pigment surface.

5. The nail enamel of claim 1 wherein the inorganic pigment is selected from the group consisting of iron oxides, titanated mica, iron oxide coated mica, titanium dioxide, ultramarine, chromium oxide, chromium hydroxide, and manganese violet.

6. In a nail enamel comprising a plurality of inorganic pigments suspended in a liquid base which comprises nitrocellulose, a solvent, and a suspending agent, the improvement wherein said inorganic pigments have a coating consisting of one or more organically substituted polysiloxanes which are chemically bonded to the pigments' surfaces, wherein said enamel exhibits reduced settling and migration of the pigments compared to an enamel which is identical except for lacking said chemically bonded coating.

7. The nail enamel of claim 6 wherein said coating, when bonded to said pigment surface, has 1–1000 (Si—O) units in which the remaining functional sites of each Si atom are substituted with hydrogen, methyl, $C_2$–$C_{30}$ alkyl, $C_2$–$C_{30}$ alkenyl, or phenyl, provided that at least one Si atom of the polysiloxanes is chemically bonded to an oxygen atom which is bonded to the pigment surface.

8. The nail enamel of claim 6 wherein the inorganic pigment is selected from the group consisting of iron oxides, titanated mica, iron oxide coated mica, titanium dioxide, ultramarine, chromium oxide, chromium hydroxide, and manganese violet.

9. The nail enamel of claim 6 wherein said coated pigment comprises up to about 10 wt. % of the nail enamel.

10. The nail enamel of claim 6 wherein said coated pigment comprises up to about 2 wt. % of the nail enamel.

11. A nail enamel consisting essentially of: (A) a plurality of pigments, including at least one inorganic pigment; and (B) a liquid base for holding said pigments in suspension, said base being of the type in which said inorganic pigment tends to migrate; wherein said inorganic pigment is in a form such that its tendency to migrate is deterred, said inorganic pigment having a coating thereon of an organically substituted polysiloxane which is bonded chemically to the surface of the pigment.

12. A nail enamel according to claim 11 including a plurality of inorganic pigments and nitrocellulose.

13. The nail enamel of claim 11 wherein said coated pigment comprises up to about 10 wt. % of the nail enamel.

14. The nail enamel of claim 11 wherein said coated pigment comprises up to about 2 wt. % of the nail enamel.

15. The nail enamel of claim 11 wherein said coating, when bonded to said pigment surface, has 1–1000 (Si—O) units in which the remaining functional sites of each Si atom are substituted with hydrogen, methyl, $C_2$–$C_{30}$ alkyl, $C_2$–$C_{30}$ alkenyl, or phenyl, provided that at least one Si atom of the polysiloxanes is chemically bonded to an oxygen atom which is bonded to the pigment surface.

16. The nail enamel of claim 11 wherein the inorganic pigment is selected from the group consisting of iron oxides, titanated mica, iron oxide coated mica, titanium dioxide, ultramarine, chromium oxide, chromium hydroxide and manganese violet.

17. A nail enamel according to claim 1, 2, 3, 4, 5, 11, 12, 13, 14, 15 or 16 including a plurality of said inorganic pigments, each of which has said coating thereon.

* * * * *